(12) United States Patent
Nagai et al.

(10) Patent No.: US 10,073,052 B2
(45) Date of Patent: Sep. 11, 2018

(54) ION CONCENTRATION SENSOR

(71) Applicants: Sharp Kabushiki Kaisha, Sakai, Osaka (JP); National University Corporation TOYOHASHI UNIVERSITY OF TECHNOLOGY, Toyohashi-shi, Aichi (JP)

(72) Inventors: Kenichi Nagai, Sakai (JP); Satoshi Saitoh, Sakai (JP); Kazuaki Sawada, Toyohashi (JP)

(73) Assignees: SHARP KABUSHIKI KAISHA, Sakai (JP); NATIONAL UNIVERSITY CORPORATION TOYOHASHI UNIVERSI, Aichi (JP)

( * ) Notice: Subject to any disclaimer, the term of this patent is extended or adjusted under 35 U.S.C. 154(b) by 130 days.

(21) Appl. No.: 15/372,693

(22) Filed: Dec. 8, 2016

(65) Prior Publication Data
US 2017/0168010 A1    Jun. 15, 2017

(30) Foreign Application Priority Data

Dec. 15, 2015 (JP) .................. 2015-244575

(51) Int. Cl.
| | | |
|---|---|---|
| G01N 27/02 | (2006.01) | |
| G01N 27/414 | (2006.01) | |
| G01N 27/416 | (2006.01) | |
| G01N 31/02 | (2006.01) | |
| G01N 27/42 | (2006.01) | |
| G01N 30/64 | (2006.01) | |
| G01N 30/34 | (2006.01) | |

(52) U.S. Cl.
CPC ..... *G01N 27/4145* (2013.01); *G01N 27/4162* (2013.01); *G01N 27/42* (2013.01); *G01N 31/02* (2013.01); *G01N 2030/345* (2013.01); *G01N 2030/645* (2013.01)

(58) Field of Classification Search
CPC ....... G01N 2030/345; G01N 2030/645; G01N 27/4162; G01N 27/42; G01N 31/02
USPC .................. 324/425, 439; 438/142; 257/414; 205/789; 422/82.03
See application file for complete search history.

(56) References Cited

U.S. PATENT DOCUMENTS

| | | |
|---|---|---|
| 6,255,678 B1 | 7/2001 | Sawada et al. |
| 2005/0062093 A1 | 3/2005 | Sawada et al. |

(Continued)

FOREIGN PATENT DOCUMENTS

| | | |
|---|---|---|
| JP | 2002-098667 A | 4/2002 |
| JP | 2005-207797 A | 8/2005 |

(Continued)

*Primary Examiner* — Jermele M Hollington
*Assistant Examiner* — Raul Rios Russo
(74) *Attorney, Agent, or Firm* — Keating & Bennett, LLP

(57) ABSTRACT

Provided is an ion sensor including a supporting substrate, a plurality of cells, a silicon substrate, a plurality of transistors, and an analog-digital conversion circuit. The plurality of cells, the plurality of transistors, and the analog-digital conversion circuit are provided above the supporting substrate. Each of the plurality of transistors has a corresponding gate provided on a first surface of the silicon substrate. The analog-digital conversion circuit is provided on the silicon substrate. The ion-sensing surface is provided on a second surface of the silicon substrate. The second surface is opposite to the first surface.

6 Claims, 8 Drawing Sheets

(56) References Cited

U.S. PATENT DOCUMENTS

| | | |
|---|---|---|
| 2005/0156207 A1 | 7/2005 | Yazawa et al. |
| 2014/0175592 A1* | 6/2014 | Iwabuchi ............ H04N 5/2253 |
| | | 257/443 |
| 2014/0264467 A1 | 9/2014 | Cheng et al. |
| 2016/0071463 A1* | 3/2016 | Takahashi ............ G09G 3/3225 |
| | | 345/76 |
| 2016/0109404 A1 | 4/2016 | Saitoh et al. |
| 2016/0255296 A1* | 9/2016 | Iwabuchi ............ H04N 5/2253 |
| | | 348/300 |

FOREIGN PATENT DOCUMENTS

| | | |
|---|---|---|
| JP | 2007-278760 A | 10/2007 |
| JP | 4195859 B2 | 12/2008 |
| JP | 4231560 B2 | 3/2009 |
| JP | 2013-011482 A | 1/2013 |
| JP | 2014-115125 A | 6/2014 |
| JP | 2016-080601 A | 5/2016 |

\* cited by examiner

10 : CELL
11 : SILICON SUBSTRATE
11a~11c : n+ DIFFUSION REGION
12 : SiO₂ FILM
13 : SURFACE FILM
14 : RESET GATE
15 : TRANSFER GATE
16 : ELECTRIC CHARGE INJECTION CONTROL GATE
Er : REFERENCE ELECTRODE
OJT : TEST OBJECT

1 : ION-SENSING ARRAY
1a : ION-SENSING SURFACE
9 : SUPPORTING SUBSTRATE
11 : SILICON SUBSTRATE
11d : n-WELL REGION
11e : p-WELL REGION
12 : $SiO_2$ FILM
13 : SURFACE FILM
15 : TRANSFER GATE
17 : MULTILAYER WIRING LAYER
18 : METALLIC WIRING
19 : PIXEL-DIVIDING SECTION
21 : PERIPHERAL CIRCUIT SECTION
21a : pMOS SECTION
21b : nMOS SECTION
22 : GATE
23 : PROTECTIVE FILM
100 : ION SENSOR

30 : CELL
31 : SILICON SUBSTRATE
32 : SiO$_2$ FILM
33 : SURFACE FILM
34 : RESET GATE
35 : TRANSFER GATE
36 : CONTROL GATE
Er : REFERENCE ELECTRODE
OJT : TEST OBJECT

10C: CELL
11 : SILICON SUBSTRATE
11a~11c: n⁺ DIFFUSION REGION
12 : SiO₂ FILM
13 : SURFACE FILM
14 : RESET GATE
15 : TRANSFER GATE
16 : ELECTRIC CHARGE INJECTION CONTROL GATE
20 : DIVIDING WALL
Er : REFERENCE ELECTRODE
OJT : TEST OBJECT

1 : ION-SENSING ARRAY
1a: ION-SENSING SURFACE
9 : SUPPORTING SUBSTRATE
10C: CELL
11 : SILICON SUBSTRATE
11d: n-WELL REGION
11e: p-WELL REGION
12 : SiO$_2$ FILM
13 : SURFACE FILM
15 : TRANSFER GATE
17 : MULTILAYER WIRING LAYER
18 : METALLIC WIRING
19 : PIXEL-DIVIDING SECTION
20 : DIVIDING WALL
21 : PERIPHERAL CIRCUIT SECTION
21a: pMOS SECTION
21b: nMOS SECTION
22 : GATE
23 : PROTECTIVE FILM
100A: ION SENSOR

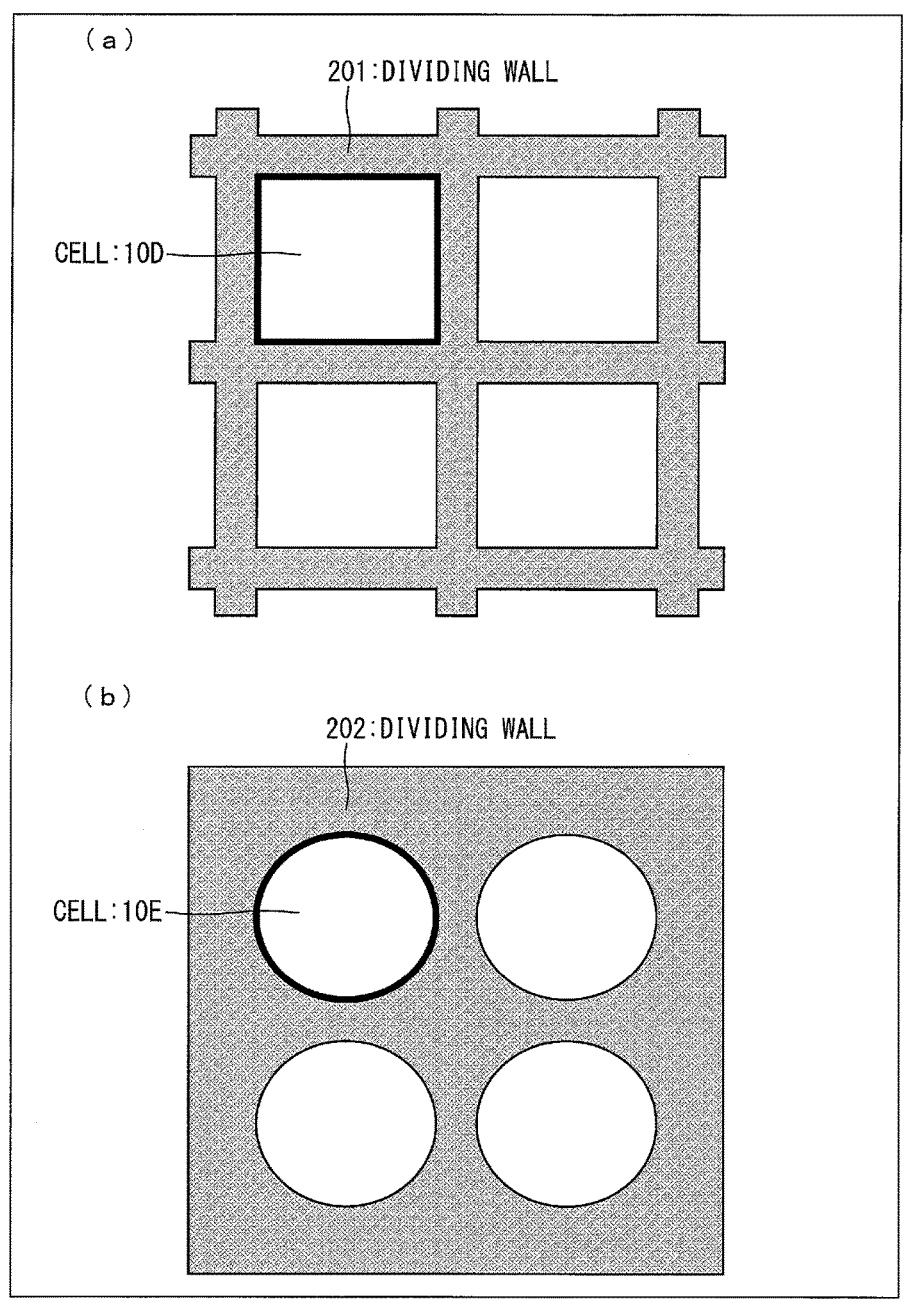

ION CONCENTRATION SENSOR

This Nonprovisional application claims priority under 35 U.S.C. § 119 on Patent Application No. 2015-244575 filed in Japan on Dec. 15, 2015, the entire contents of which are hereby incorporated by reference.

TECHNICAL FIELD

The present invention relates to an ion concentration sensor for detecting an ion concentration of a test object.

BACKGROUND ART

Conventional ion concentration sensors of FET type, such as an ion sensitive field effect transistor (ISFET) for detecting hydrogen ion concentration, have problems of low sensitivity, temporally variable outputs, and the like. In order to address such problems, for example, there has been proposed an FET ion sensor for detecting an amount of change in channel electric potential, which varies in accordance with change in surface electric potential of a sensing section (see Patent Literatures 1 through 4).

A surface of the above sensing section is typically covered with a silicon nitride film. Such a sensing section is configured to detect a hydrogen ion concentration through the use of change in surface electric potential of a semiconductor substrate, which change is caused by a reaction of (i) dangling bonds and (ii) hydrogen ions on a surface of the silicon nitride film. Each of FET ion sensors disclosed in respective Patent Literatures 1 through 4 is configured to output, as an analog signal, to external devices, an amount of change in electric potential which varies in accordance with hydrogen ion concentration.

CITATION LIST

Patent Literature

[Patent Literature 1]
Japanese Patent No. 4195859 (issued on Dec. 17, 2008)
[Patent Literature 2]
Japanese Patent Application Publication, Tokukai, No. 2002-98667 (Publication date: Apr. 5, 2002)
[Patent Literature 3]
Japanese Patent Application Publication, Tokukai, No. 2007-278760 (Publication date: Oct. 25, 2007)
[Patent Literature 4]
Japanese Patent No. 4231560 (issued on Dec. 17, 2008)

SUMMARY OF INVENTION

Technical Problem

In a production of the conventional FET ion sensor, it is necessary for a surface of the silicon nitride film to be exposed in the last step of such a production. This is because the sensing section employs a silicon nitride film as a sensing film. In order for the surface of the silicon nitride film to be exposed, it is necessary (i) for no wiring to be provided on an uppermost surface of the silicon nitride film and (ii) for another insulating film (e.g., silicon oxide film), on the silicon nitride film, to be formed so as to have a thickness which allows another insulating film to be stably etched, i.e., for another insulating film to be as thin as possible.

From the viewpoint of practicality, it is desirable that a FET sensor be provided in a form of a system-on-chip in which (i) the FET sensor and (ii) a circuit section including an analog-digital converter, a digital circuit, and the like are provided on a single chip. In such a system-on-chip, (i) an ion-sensing array in which sensing sections are provided in an array manner and (ii) the circuit section are provided on a single surface of the chip. Because of this, it is necessary to (i) provide basic configuration elements, constituting the circuit section (e.g., a flip-flop, an inverter, a capacitor, etc.), outside the region in which the ion-sensing array is provided and (ii) connect the ion-sensing array to the circuit section.

Such a connection necessitates a multilayer wiring structure in which wirings for connecting the ion-sensing array to the circuit section are provided in one or more layers. A wiring structure consisting of two or less layers suffices for a case where an ion sensor outputs an analog signal. Meanwhile, in a case where an ion sensor outputs a digital signal, a wiring structure consisting of four to six layers is needed.

However, conventional FET ion sensors are each configured such that the surface of the silicon nitride film is exposed as described earlier, so that the multilayer wiring structure is provided around the ion-sensing array. Particularly, an ion sensor, which outputs a digital signal, needs to have a thick multilayer wiring structure. However, it is not preferable to provide such a thick multilayer wiring structure around the ion-sensing array. Under restrictions on production process, it is only possible to provide, as the ion sensitive film, a silicon nitride film.

The present invention has been accomplished in view of the above problem, and an object of an aspect of the present invention is to provide an ion concentration sensor realized by a structure of system-on-chip.

Solution to Problem

In order to attain the above object, an ion concentration sensor in accordance with an aspect of the present invention includes: a supporting substrate; a plurality of sensing sections having a sensing surface with which a test object is to be brought into contact, each of the plurality of sensing sections being sensitive to ions of the test object; a semiconductor layer provided between the supporting substrate and the plurality of sensing sections; a plurality of transistors which are configured to read out and transfer respective analog signals which vary in accordance with amounts of ions sensed by the respective plurality of sensing sections; and an analog to digital conversion circuit which converts, into respective digital signals, the analog signals transferred from the respective plurality of transistors, the plurality of sensing sections, the plurality of transistors, and the analog to digital conversion circuit being provided above the supporting substrate, the plurality of transistors being provided on the semiconductor layer, each of the plurality of transistors having a corresponding gate provided on a first surface of the semiconductor layer, the analog to digital conversion circuit being provided on the semiconductor layer, the sensing surface being provided on a second surface of the semiconductor layer, the second surface being opposite to the first surface.

Advantageous Effects of Invention

An aspect of the present invention makes it possible to provide an ion concentration sensor realized by a structure of system-on-chip.

Figure 2:
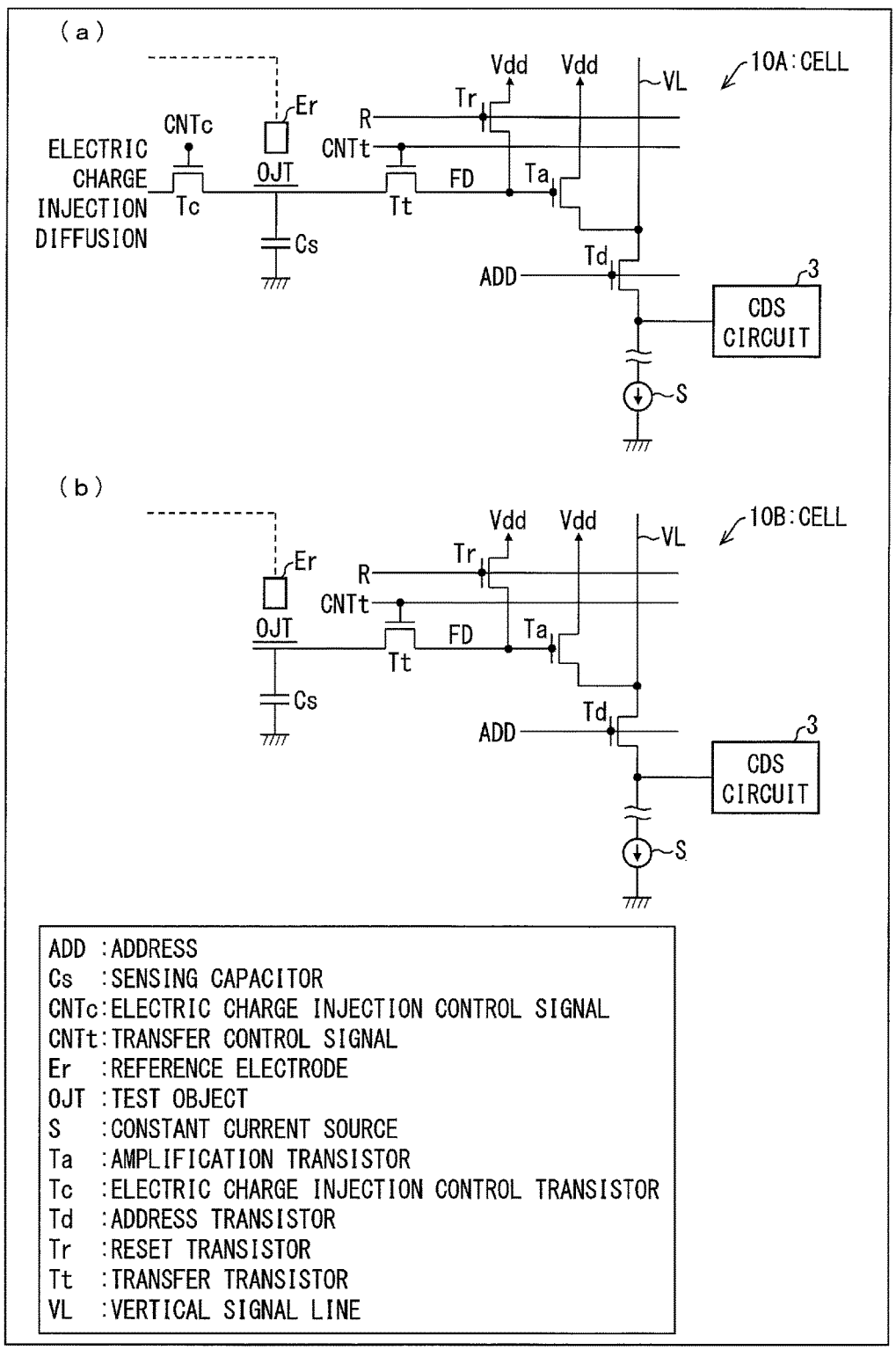

(a) of FIG. 2 is an equivalent circuit diagram illustrating part of a configuration of a cell provided in an ion-sensing array of the ion sensor. (b) of FIG. 2 is an equivalent circuit diagram illustrating a configuration of another cell provided in the ion-sensing array.

Figure 3:
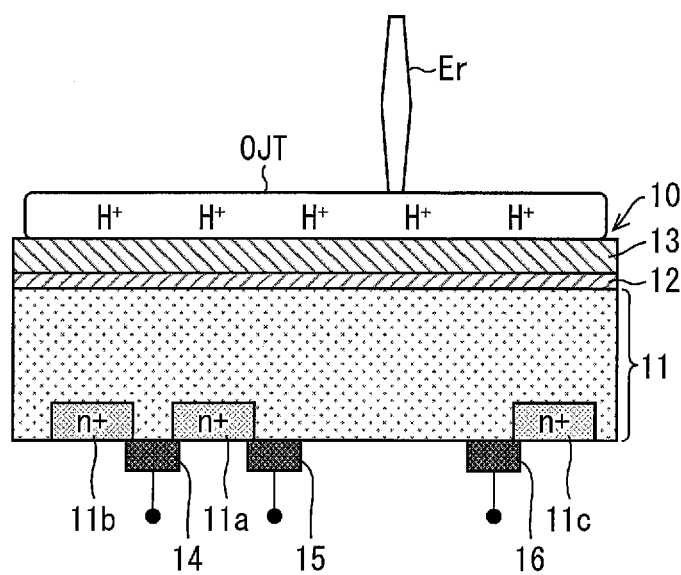

FIG. 3 is a vertical cross-sectional view illustrating a configuration of the cell provided in the ion-sensing array.

Figure 4:
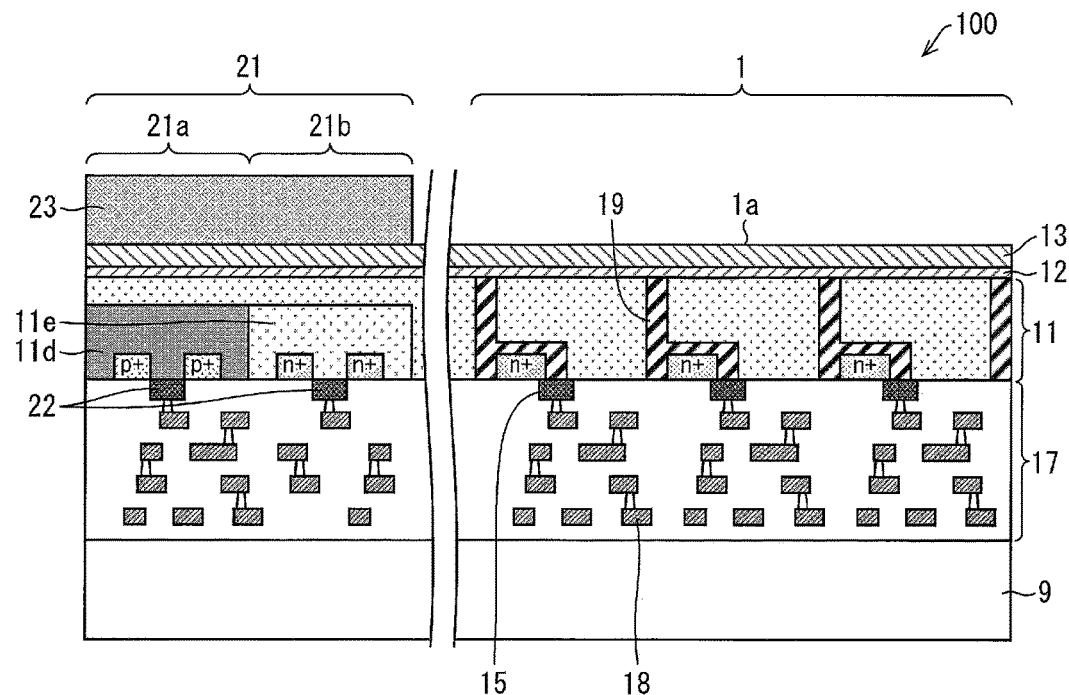

FIG. 4 is a vertical cross-sectional view illustrating configurations of respective of the ion-sensing array and a peripheral circuit section.

Figure 5:
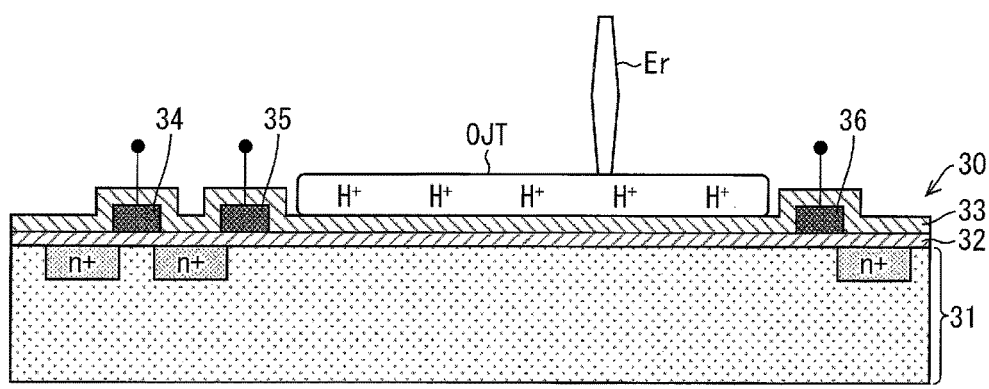

FIG. 5 is a vertical cross-sectional view illustrating how a cell is provided in an ion-sensing array of an ion sensor in accordance with Comparative Example.

Figure 6:
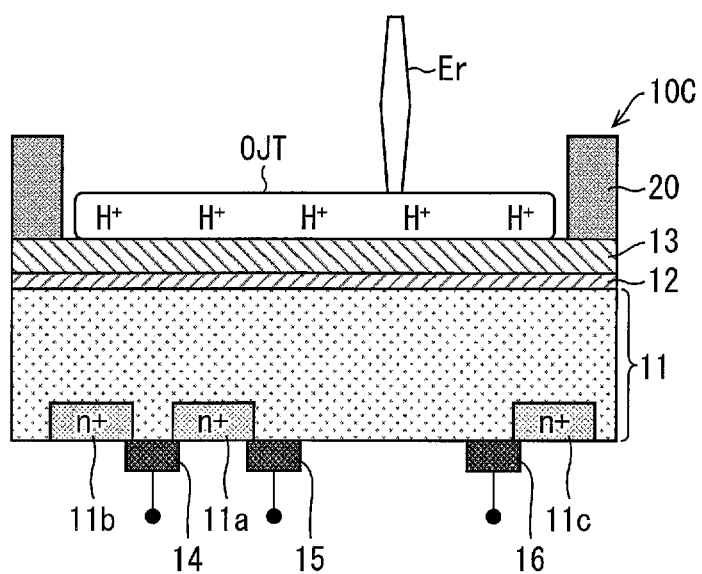

FIG. 6 is a vertical cross-sectional view illustrating how a sensing section, which is a cell, is provided in an ion-sensing array of an ion sensor in accordance with Embodiment 2 of the present invention.

Figure 7:
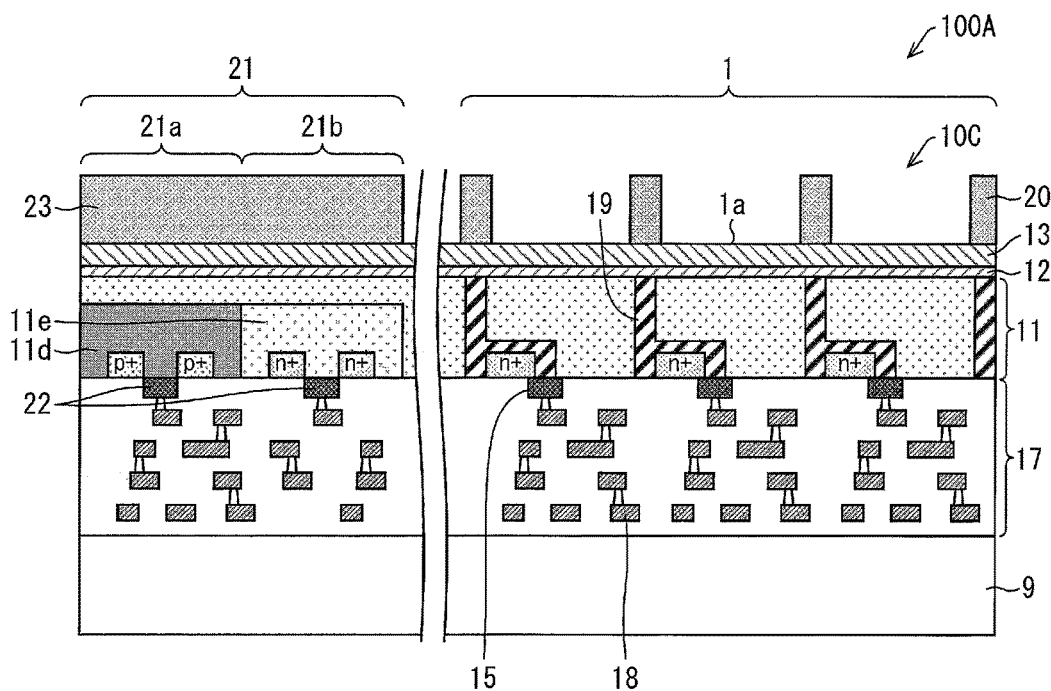

FIG. 7 is a vertical cross-sectional view illustrating configurations of respective of the ion-sensing array illustrated in FIG. 6 and a peripheral circuit section.

Each of (a) and (b) of FIG. 8 is a plan view illustrating a structure for dividing cells of an ion sensor in accordance with Embodiment 3 of the present invention.

DESCRIPTION OF EMBODIMENTS

Embodiment 1

The following description will discuss Embodiment 1 of the present invention with reference to FIGS. 1 through 5.

<Configuration of Ion Sensor 100>

Figure 1:
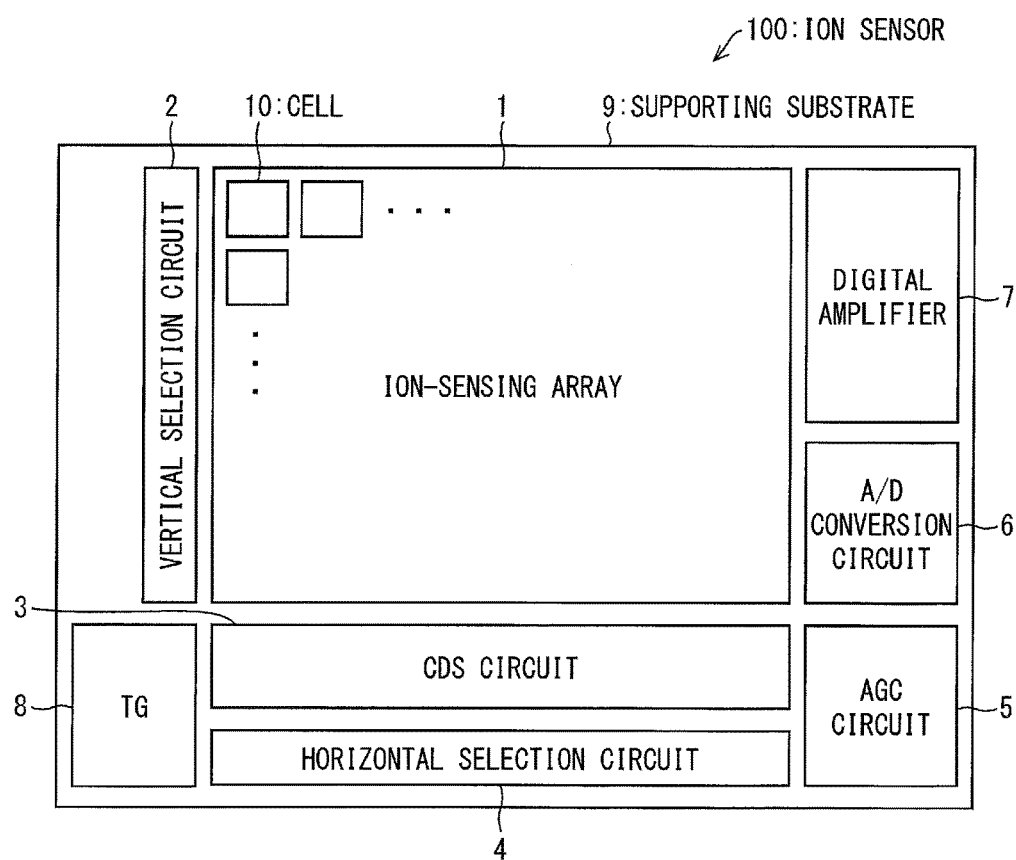
FIG. 1 is a plan view illustrating a configuration of an ion sensor in accordance with Embodiment 1 of the present invention.

FIG. 1 is a plan view illustrating a configuration of an ion sensor 100 in accordance with Embodiment 1.

As illustrated in FIG. 1, the ion sensor 100 (ion concentration sensor) includes at least (i) an ion-sensing array 1, (ii) a vertical selection circuit 2, (iii) a correlated double sampling (CDS) circuit 3, (iv) a horizontal selection circuit 4, (v) an automatic gain control (AGC) circuit 5, (vi) an A/D conversion circuit 6 (analog to digital conversion circuit), (vii) a digital amplifier 7, and (viii) a timing generator 8, which is indicated as "TG" in FIG. 1. Such components are provided on a single supporting substrate 9 (chip).

The ion-sensing array 1 includes plenty of cells 10 (sensing sections) of CMOS type, which are provided in a two-dimensional array manner (matrix manner) and each made of a complementary metal oxide semiconductor (CMOS).

The ion-sensing array 1 includes (i) a plurality of address lines, which are provided in rows for selecting the cells 10 row by row, and (ii) a plurality of vertical signal lines, which are provided in columns for selecting the cells 10 column by column. In order to respond to ions, there is provided on each of the cells 10, as a surface layer, a silicon nitride film made of silicon nitride ($Si_3N_4$), an aluminum oxide film made of aluminum oxide ($Al_2O_3$), or a tantalm oxide film made of tantalm oxide ($Ta_2O_5$). Each of the cells 10 quantitatively detects hydrogen ions based on change in diode electric potential which varies in accordance with increase and decrease in dangling bonds on the surface film. The ion sensor 100 is also an ion sensor of X-Y address type which detects an amount of change in channel electric potential which varies in accordance with change in surface electric potential of each of the cells 10.

The vertical selection circuit 2 is configured to supply selection signals (address signals) for switching on and/or off transistors (see address transistors Td illustrated in (a) of FIG. 2 and described later) that connect or disconnect between the vertical signal lines and the CDS circuit 3 such that the cells 10 are sequentially selected column by column.

The CDS circuit 3 includes (i) a first sample-and-hold circuit configured to hold signal levels of signals supplied from the respective cells 10 selected by the vertical selection circuit 2, (ii) a second sample-and-hold circuit configured to hold zero levels of the respective signals, and (iii) a subtractor. The subtractor subtracts the zero levels, outputted by the second sample-and-hold circuit, from the signal levels, outputted by the first sample-and-hold circuit. As such, the CDS circuit 3 removes fixed-pattern noises of the respective cells 10.

The horizontal selection circuit 4 is configured to sequentially select, row by row, the signals from which the respective fixed-pattern noises have been removed by the CDS circuit 3.

The AGC circuit 5 is configured to amplify, at an appropriate gain, the signals supplied from the horizontal selection circuit 4.

The A/D conversion circuit 6 is configured to convert, into digital signals, respective analog signals supplied from the AGC circuit 5.

The digital amplifier 7 is configured to appropriately amplify the digital signals supplied from the A/D conversion circuit 6.

The timing generator 8 is configured to generate various timing signals, based on which each of the vertical selection circuit 2, the CDS circuit 3, the horizontal selection circuit 4, the AGC circuit 5, the A/D conversion circuit 6, and the digital amplifier 7 operates.

<Circuit Configuration of First Cell>

(a) of FIG. 2 is an equivalent circuit diagram illustrating a configuration of a cell 10A (first cell) provided in the ion-sensing array 1 of the ion sensor 100.

As illustrated in (a) of FIG. 2, the cell 10A has a sensing capacitor Cs serving as an ion-sensing element. The cell 10A also includes (i) an electric charge injection control transistor Tc, (ii) a transfer transistor Tt, (iii) an amplification transistor Ta, (iv) an address transistor Td, and (v) a reset transistor Tr, each serving as an active element. The transistors (i) through (v) are each a metal oxide semiconductor field effect transistor (MOSFET).

The cell 10A further includes a reference electrode Er, which is an electrode defining a reference electric potential. A silver-silver chloride electrode is typically employed as the reference electrode Er. The reference electrode Er has an electric potential of +0.222 V at 25° C. Ionization of a test object OJT causes an interface electric potential between the test object OJT and the ion sensitive film, on the basis that an electric potential of the reference electrode Er is a reference electric potential.

An electric charge injection control signal CNTc is supplied to the gate of the electric charge injection control transistor Tc. Electric charges are injected to a source of the electric charge injection control transistor Tc. A drain of the electric charge injection control transistor Tc is connected to (i) one electrode (cathode) of the sensing capacitor Cs and (ii) a source of the transfer transistor Tt. The other electrode (anode) of the sensing capacitor Cs is grounded. The test object OJT is to be placed above the sensing capacitor Cs.

A drain of the transfer transistor Tt is connected to (i) a gate of the amplification transistor Ta and (ii) a source of the reset transistor Tr. The gate of the amplification transistor Ta forms a floating diffusion section FD. A transfer control signal CNTt is supplied to a gate of the transfer transistor Tt. A reset signal R is supplied to the gate of the reset transistor Tr. A power-supply voltage Vdd is supplied to each of the respective drains of the amplification transistor Ta and the reset transistor Tr. A vertical signal line VL is supplied to a source of the amplification transistor Ta. A drain of the address transistor Td is connected to the vertical signal line VL, and a source of the address transistor Td is connected to an input terminal of the CDS circuit 3. An address signal ADD is supplied to a gate of the address transistor Td. A constant current source S is provided between a ground and the source of the address Transistor Td.

<Circuit configuration of second cell>

(b) of FIG. 2 is an equivalent circuit diagram illustrating how a cell 10B (second cell), which is different from the cell 10A, is provided in the ion-sensing array 1 of the ion sensor 100.

As illustrated in (b) of FIG. 2, the cell 10B differs from the cell 10A in that it does not include an electric charge injection control transistor Tc. Namely, the cell 10B differs from the cell 10A in that the reset transistor Tr injects electric charges into the sensing capacitor Cs.

<Cross-Section Structure of Cell>

FIG. 3 is a vertical cross-sectional view illustrating part of a configuration of the cell 10 provided in the ion-sensing array 1 of the ion sensor 100.

As illustrated in FIG. 3, the cells 10 includes a silicon substrate 11 (semiconductor layer), an $SiO_2$ film 12, and a surface film 13.

The silicon substrate 11 is made of p-type silicon. A $SiO_2$ film 12 is provided on one side of the silicon substrate 11. A surface film 13 is provided on the $SiO_2$ film 12. The silicon substrate 11 is prepared by polishing a silicon wafer through chemical mechanical polishing (CMP) so that a silicon layer has a thickness of approximately 1 μm to 10 μm. The surface film 13 is made of $Si_3N_4$, $Al_2O_3$, or $Ta_2O_5$. The $SiO_2$ film 12 and the surface film 13 serve as an ion-sensing surface.

A reset gate 14, a transfer gate 15, an electric charge injection control gate 16, and an address gate (not illustrated) are provided on the other surface of the silicon substrate 11. The reset gate 14 serves as the gate of the reset transistor Tr. The transfer gate 15 serves as the gate of the transfer transistor Tt. The electric charge injection control gate 16 serves as the gate of the electric charge injection control transistor Tc. The address gate serves as the gate of the address transistor Td. In the silicon substrate 11, an n+diffusion region 11a, serving as the floating diffusion section FD, is provided between the reset gate 14 and the transfer gate 15. In the silicon substrate 11, (i) an $n^+$ diffusion region 11b, serving as the drain of the reset transistor Tr, and (ii) an $n^+$ diffusion region 11c, serving as the drain of the electric charge injection control transistor Tc, are provided.

According to the sensing sections, the ion-sensing surface is provided on a surface of one side (second surface) of the silicon substrate 11. The reset gate 14, the transfer gate 15, and the electric charge injection control gate 16 are provided on a surface of the other side (first surface) of the silicon substrate 11, the other side being opposite to the ion-sensing surface.

<Operation of Cell>

Operation of the cell 10A will be discussed below.

In a case where an active electric charge injection control signal CNTc is supplied to the gate of the electric charge injection control transistor Tc, the electric charge injection control transistor Tc is turned on, so as to inject electric charges into the sensing capacitor Cs. Then, in a case where a test object OJT comes into contact with the ion-sensing surface, a p-type silicon region of the silicon substrate 11, which region is constituted by the sensing capacitor Cs, causes change in electric potential in accordance with an amount of hydrogen ions that are to be detected with regard to the test object OJT. The transfer transistor Tt transfers, to the floating diffusion section FD, the electric charges that have been accumulated in the sensing capacitor Cs. The amplification transistor Ta converts, into a voltage, an amount of the electric charges thus transferred. This causes the amount of the electric charges, which amount varies in accordance with the change in electric potential, to be detected as a voltage. In other words, this causes a signal, which varies in accordance with an amount of ions, to be read out.

In a case where the address transistor Td is turned on in response to the gate of the address transistor Td receiving the address signal ADD, the cells 10A is selected. This causes the voltage, which has been converted by the amplification transistor Ta, to be transmitted to the CDS circuit 3 via the vertical signal line VL.

The reset transistor Tr resets, in response to the reset signal R supplied to the gate thereof, the electric potential of the floating diffusion section FD to the power-supply voltage Vdd.

<Multilayer Wiring Structure>

FIG. 4 is a vertical cross-sectional view illustrating configurations of respective of the ion-sensing array 1 and a peripheral circuit section of the ion sensor 100. Note that FIG. 4 illustrates a cross-sectional structure in which, of the reset gate 14, the transfer gate 15, and the electric charge injection control gate 16 illustrated in FIG. 3, only the transfer gate 15 can be observed.

As illustrated in FIG. 4, the ion sensor 100 is configured such that (i) a multilayer wiring layer 17 is provided on the supporting substrate 9 and (ii) the silicon substrate 11 is provided on the multilayer wiring layer 17. The multilayer wiring layer 17 includes (i) a plurality of metallic wirings 18 that are hierarchically provided and (ii) a filling material ($SiO_2$) that fills a space between the respective plurality of metallic wirings 18 in a hierarchical manner. In the multilayer wiring layer 17, (i) the plurality of metallic wirings 18 are separately provided on a plurality of (three or more) layers so as to transmit digital signals and (ii) some of the plurality of metallic wirings 18, which are provided in different layers, are electrically connected. Note that each of the metallic wirings 18 is made of Al or Cu.

As described earlier, the $SiO_2$ film 12 and the surface film 13 are provided on the silicon substrate 11. The surface of the surface film 13 constitutes an ion-sensing surface 1a (sensing surface) of the ion-sensing array 1, with which surface the test object is to be brought into contact.

The ion sensor 100 can be divided into the ion-sensing array 1 and a peripheral circuit section 21. The peripheral circuit section 21 includes the vertical selection circuit 2, the CDS circuit 3, the horizontal selection circuit 4, the AGC circuit 5, the A/D conversion circuit 6, the digital amplifier 7, and the timing generator 8.

In the ion-sensing array 1, the reset gate 14, the transfer gate 15, the electric charge injection control gate 16, and the address gate (not illustrated in FIG. 4) are provided so as to be located on a surface (first surface) of the multilayer wiring layer 17, which surface is on a side of the silicon substrate 11. Note that FIG. 4 illustrates a configuration in which only the transfer gate 15 is located on such a side.

Some of the plurality of metallic wirings 18 provided on an uppermost layer of the multilayer wiring layer 17 are connected to the reset gate 14, the transfer gate 15, the electric charge injection control gate 16, and the address gate so as to supply corresponding signals to the respective gates. A region of the ion-sensing array 1 of the silicon substrate 11 is divided into cells by using pixel-dividing sections 19.

In a region of the peripheral circuit section 21 of the silicon substrate 11, a n-well region 11d and a p-well region 11e are provided so as to be adjacent to each other. Plural pairs of $p^+$ diffusion regions are provided in the n-well region 11d, and plural pairs of $n^+$ diffusion regions are provided in the p-well region 11e. Each pair of the $p^+$ diffusion regions and of the $n^+$ diffusion regions has a gate that is provided so as to be located on a surface of the multilayer wiring layer 17, which surface is on a side of the silicon substrate 11. Such a gate is connected to part of the plurality of metallic wirings 18 that are provided on the uppermost layer of the multilayer wiring layer 17.

Transistors (pMOS transistors and nMOS transistor) are thus provided on the silicon substrate 11. The pMOS transistors are provided in a pMOS section 21a of the peripheral circuit section 21, and the nMOS transistors are provided in an nMOS section 21b of the peripheral circuit section 21. Each of the vertical selection circuit 2, the CDS circuit 3, the horizontal selection circuit 4, the AGC circuit 5, the A/D conversion circuit 6, the digital amplifier 7, the timing generator 8, and the like is realized by appropriately combining a plurality of pMOS sections 21a and nMOS sections 21b.

A protective film 23 is provided on the surface film 13 in the peripheral circuit section 21. The protective film 23 is made of $Si_3N_4$, $Al_2O_3$, or $Ta_2O_5$, as with the surface film 13.

COMPARATIVE EXAMPLE

Comparative Example of Embodiment 1 will be discussed below. FIG. 5 is a vertical cross-sectional view illustrating how a cell is provided in an ion-sensing array of an ion sensor in accordance with Comparative Example of Embodiment 1.

According to a cell 30 in accordance with Comparative Example, a $SiO_2$ film 32 is provided on a silicon substrate 31 (see FIG. 5). A reset gate 34, a transfer gate 35, and an electric charge injection control gate 36 are provided around an ion-sensing surface, on which a test object OJT is to be placed, of the $SiO_2$ film 32. The reset gate 34, the transfer gate 35, and the electric charge injection control gate 36 have functions identical to functions of respective of the reset gate 14, the transfer gate 15, and the electric charge injection control gate 16.

With the configuration of the cell 30, the reset gate 34, the transfer gate 35, the electric charge injection control gate 36, and the ion-sensing surface are provided on the same surface of the silicon substrate 31. This increases the cells 30 in area.

<Effect of Ion Sensor 100>

The ion sensor 100 is an ion sensor of X-Y address type, which detects an amount of change in channel electric potential, which varies in accordance with change in surface electric potential of the cells 10. This makes it possible to provide an ion sensor that can achieve a high signal-to-noise ratio and that can read out signals at a high speed. Such an ion sensor can bring about finding of local activities and/or behavior of a single microscopic cell such as an i-PS cell. It can be said that humans have three billions of DNAs, 500 million of which are disease-related DNAs. However, use of the ion sensor 100 makes it possible to simultaneously measure twenty millions of cells in a chip of approximately 7 mm square. This allows base sequence analysis to be completed in a short time.

Moreover, the ion sensor 100 is configured such that the ion-sensing array 1 and the peripheral circuit section 21 are provided on the same silicon substrate 11. The ion-sensing surface 1a is located on a surface (second surface) of a second side of the silicon substrate 11, on which side the $SiO_2$ film 12 and the surface film 13 are provided. Various gates, such as the transfer gate 15, are provided on a surface (first surface) of a first side opposite to the second side of the silicon substrate 11.

The above structure allows (i) the ion-sensing surface 1a to have a sufficiently wide area while reducing size of the cell 10 to 10 μm or less and (ii) the multilayer wiring layer 17 to be provided on the second side. This ultimately allows the ion sensor 100 to be downsized despite including the peripheral circuit section 21. As such, it is possible to easily provide the ion sensor 100 realized by a structure of system-on-chip.

Since the multilayer wiring layer 17 is not provided on the second surface, the production process is free from constraints. This makes it possible to employ, as the ion sensitive film, an aluminum oxide film or a tantalm oxide film other than a typically-employed silicon nitride film. Note that, though aluminum oxide and tantalm oxide are superior in ion sensitivity to silicon nitride, these oxides lack in practicality in view of productivity, processability, and material cost of a resultant film. Thus, in a case where ion sensitivity is emphasized, it is preferable that the ion sensor 100 include an ion sensitive film made of aluminum oxide or tantalm oxide.

The multilayer wiring layer 17 has a layer structure which has the metallic wirings 18 of three or more layers. Note that a typical digital circuit needs to have a layer structure which has wirings of not less than four layers and not more than six layers. Since the multilayer wiring layer 17 of the ion sensor 100 has the metallic wiring 18 of not less than four layers and not more than six layers, the A/D conversion circuit 6 is provided on the silicon substrate 11 so that an ion detection result is outputted in a form of digital signal. The ion sensor 100 can further include a desirable digital circuit that processes a digital signal supplied from the A/D conversion circuit 6.

Embodiment 2

The following description will discuss Embodiment 2 of the present invention with reference to FIGS. 6 and 7. Note that in Embodiment 2, components having functions identical to equivalent components in Embodiment 1 are given identical reference numerals, and descriptions thereof are omitted.

FIG. 6 is a vertical cross-sectional view illustrating how a cell 10C is provided in an ion-sensing array 1 of an ion sensor 100A in accordance with Embodiment 2. FIG. 7 is a vertical cross-sectional view illustrating configurations of respective of the ion-sensing array 1 and a peripheral circuit section 21 of the ion sensor 100A in accordance with Embodiment 2.

As illustrated in FIG. 7, the ion sensor 100A is identical to the ion sensor 100 illustrated in FIG. 4, except that the cells 10C illustrated in FIG. 6 are separated from each other by dividing walls 20 (walls). Each of the dividing walls 20 is a wall-shaped part that is provided, on a surface film 13, by using $SiO_2$ or the like.

The cells 10C are thus separated from each other by the dividing walls 20. This makes it possible to extensively make parallel analyses of DNAs while placing different DNA templates on the respective cells 10C. It is therefore possible to suitably use the ion sensor 100A for DNA analysis.

Embodiment 3

The following description will discuss Embodiment 3 of the present invention with reference to FIG. 8. Note that in Embodiment 3, components having functions identical to equivalent components in Embodiments 1 and 2 are given identical reference numerals, and descriptions thereof are omitted.

Each of (a) and (b) of FIG. 8 is a plan view illustrating a structure for dividing cells of an ion sensor in accordance with Embodiment 3.

Embodiment 3 is applicable to the ion sensor 100A in accordance with Embodiment 2.

As illustrated in (a) of FIG. 8, cells 10D each have a square shape and are separated from each other by a dividing wall 201. This makes it possible for the cell 10D to secure a maximum area.

Meanwhile, cells 10E each have an oval shape (possibly, a round shape) and are separated from each other by a dividing wall 202 (see (b) of FIG. 8). This makes the cell 10E smaller in area than the cell 10D, but makes it possible to thicken the dividing wall 202 as compared with the dividing wall 201. It is therefore possible to reduce interference of the cells 10E.

Note that the shape of cells is, of course, not limited to the square shape or the oval shape.

[Main Points]

An ion concentration sensor in accordance with a first aspect of the present invention includes: a supporting substrate 9; a plurality of sensing sections (cells 10) having a sensing surface (ion-sensing surface 1a) with which a test object OJT is to be brought into contact, each of the plurality of sensing sections being sensitive to ions of the test object OJT; a semiconductor layer (silicon substrate 11) provided between the supporting substrate 9 and the plurality of sensing sections; a plurality of transistors (electric charge injection control transistor Tc, transfer transistor Tt, amplification transistor Ta, address transistor Td, and reset transistor Tr) which are configured to read out and transfer respective analog signals which vary in accordance with amounts of ions sensed by the respective plurality of sensing sections; and an analog to digital conversion circuit (A/D conversion circuit 6) which converts, into respective digital signals, the analog signals transferred from the respective plurality of transistors, the plurality of sensing sections, the plurality of transistors, and the analog to digital conversion circuit being provided above the supporting substrate 9, the plurality of transistors being provided on the semiconductor layer, each of the plurality of transistors having a corresponding gate provided on a first surface of the semiconductor layer, the analog to digital conversion circuit being provided on the semiconductor layer, the sensing surface being provided on a second surface of the semiconductor layer, the second surface being opposite to the first surface.

According to the above configuration, the gate of each of the plurality of transistors is provided on the first surface of the semiconductor layer, while the sensing surface is provided on the second surface of the semiconductor layer. This makes it possible to (i) reduce the plurality of sensing section in size while allowing the sensing surface to have a sufficiently wide area, and (ii) allow the multilayer wiring structure, which has wirings connected to the gate, to be provided so as to be adjacent to the second surface. Thus, the ion concentration sensor can be downsized despite including the analog to digital conversion circuit. It is therefore possible to easily provide the ion concentration sensor realized by a structure of system-on-chip.

In a second aspect of the present invention, the ion concentration sensor can further include, in the first aspect of the present invention, a multilayer wiring layer 17 provided between the supporting substrate 9 and the semiconductor layer, the multilayer wiring layer having wirings for transmitting, to the analog to digital conversion circuit, the analog signal(s) transferred from part of the plurality of transistors, the multilayer wiring layer having a layer structure which has the wirings of not less than four layers.

According to the above configuration, the ion concentration sensor further includes the multilayer wiring layer including four or more layers, so that it is possible to easily provide the ion concentration sensor with a digital circuit. This makes it possible to incorporate, into the ion concentration sensor, an intended digital circuit that can process a digital signal supplied from the analog-digital conversion circuit.

In a third aspect of the present invention, the ion concentration sensor can be arranged such that, in the first or second aspect of the present invention, the plurality of sensing sections are provided in a matrix manner; and the semiconductor layer includes a vertical selection circuit 2 and a horizontal selection circuit 4, the vertical selection circuit 2 selecting the plurality of sensing sections row by row, the horizontal selection circuit 4 outputting, column by column, the analog signals supplied from respective sensing sections that are selected by the vertical selection circuit 2.

According to the above configuration, the ion concentration sensor further includes the vertical selection circuit 2 and the horizontal selection circuit 4, so that it is unnecessary to (i) externally provide the vertical selection circuit 2 and the horizontal selection circuit 4 and (ii) connect them to the ion concentration sensor. This makes it possible to easily provide an ion concentration sensor realized by a structure of system-on-chip.

In a fourth aspect of the present invention, the ion concentration sensor can be arranged such that, in any one of the first to third aspects of the present invention, the plurality of the sensing sections are separated from each other by a wall.

The above configuration makes it possible to extensively make parallel analyses of DNAs while placing different DNA templates on the respective sensing sections. It is therefore possible to suitably use the ion concentration sensor for DNA analysis.

In a fifth aspect of the present invention, the ion concentration sensor can be arranged such that, in any one of the first to fourth aspects of the present invention, each of the plurality of sensing sections is made of a silicon nitride film, an aluminum oxide film, or a tantalm oxide film.

Since the gate is not provided on the second surface according to the first aspect, the production process is free from constraints caused in a case where the gate is provided on the second surface. This makes it possible to employ, as the ion sensitive film, other than a traditional silicon nitride film, an aluminum oxide film or a tantalm oxide.

In a sixth aspect of the present invention, the ion concentration sensor can be arranged such that, in any one of the first to fifth aspects of the present invention, an amount of change in channel electric potential is detected, the change varying in accordance with change in electric potential of the sensing surface.

With the above configuration, it is possible to provide an ion sensor that can achieve a high signal-to-noise ratio and that can read out signals at a high speed.

The present invention is not limited to the embodiments, but can be altered by a skilled person in the art within the scope of the claims. An embodiment derived from a proper combination of technical means each disclosed in a different embodiment is also encompassed in the technical scope of the present invention. Further, it is possible to form a new technical feature by combining the technical means disclosed in the respective embodiments.

REFERENCE SIGNS LIST

1 Ion-sensing array
1a Ion-sensing surface (sensing surface)
6 A/D conversion circuit (analog to digital conversion circuit)
9 Supporting substrate
11 Silicon substrate
10, 10A through 10E Cell (sensing section)
14 Reset gate (gate)
15 Transfer gate (gate)
16 Electric charge injection control gate (gate)
17 Multilayer wiring layer
20 Dividing wall (wall)
100 Ion sensor
201, 202 Dividing wall (wall)

The invention claimed is:

1. An ion concentration sensor, comprising:
a supporting substrate;
a plurality of sensing sections having a sensing surface with which a test object is to be brought into contact, each of the plurality of sensing sections being sensitive to ions of the test object;
a semiconductor layer provided between the supporting substrate and the plurality of sensing sections;
a plurality of transistors which are configured to read out and transfer respective analog signals which vary in accordance with amounts of ions sensed by the respective plurality of sensing sections; and
an analog to digital conversion circuit which converts, into respective digital signals, the analog signals transferred from the respective plurality of transistors, the plurality of sensing sections, the plurality of transistors, and the analog to digital conversion circuit being provided above the supporting substrate,
the plurality of transistors being provided on the semiconductor layer,
each of the plurality of transistors having a corresponding gate provided on a first surface of the semiconductor layer,
the analog to digital conversion circuit being provided on the semiconductor layer,
the sensing surface being provided on a second surface of the semiconductor layer, the second surface being opposite to the first surface.

2. An ion concentration sensor as set forth in claim 1, further comprising:
a multilayer wiring layer provided between the supporting substrate and the semiconductor layer,
the multilayer wiring layer having wirings for transmitting, to the analog to digital conversion circuit, the analog signal(s) transferred from part of the plurality of transistors, the multilayer wiring layer having a layer structure which has the wirings of not less than four layers.

3. An ion concentration sensor as set forth in claim 1, wherein:
the plurality of sensing sections are provided in a matrix manner; and
the semiconductor layer includes a vertical selection circuit and a horizontal selection circuit,
the vertical selection circuit selecting the plurality of sensing sections row by row,
the horizontal selection circuit outputting, column by column, the analog signals supplied from respective sensing sections that are selected by the vertical selection circuit.

4. An ion concentration sensor as set forth in claim 1, wherein:
the plurality of the sensing sections are separated from each other by a wall.

5. An ion concentration sensor as set forth in claim 1, wherein:
each of the plurality of sensing sections is made of a silicon nitride film, an aluminum oxide film, or a tantalm oxide film.

6. An ion concentration sensor as set forth in claim 1, wherein an amount of change in channel electric potential is detected, the change varying in accordance with change in electric potential of the sensing surface.

* * * * *

UNITED STATES PATENT AND TRADEMARK OFFICE
CERTIFICATE OF CORRECTION

PATENT NO. : 10,073,052 B2  
APPLICATION NO. : 15/372693  
DATED : September 11, 2018  
INVENTOR(S) : Kenichi Nagai et al.

Page 1 of 1

It is certified that error appears in the above-identified patent and that said Letters Patent is hereby corrected as shown below:

On the Title Page

Item (73), should read as follows:  
-- SHARP KABUSHIKI KAISHA, Sakai (JP); NATIONAL UNIVERSITY CORPORATION TOYOHASHI UNIVERSITY OF TECHNOLOGY, Aichi (JP) --

Signed and Sealed this  
Thirtieth Day of July, 2019

Andrei Iancu  
*Director of the United States Patent and Trademark Office*